United States Patent
Riaziat et al.

(10) Patent No.: US 7,204,254 B2
(45) Date of Patent: Apr. 17, 2007

(54) MARKERS AND SYSTEMS FOR DETECTING SUCH MARKERS

(75) Inventors: Majid L. Riaziat, San Jose, CA (US); Marcel Marc, San Jose, CA (US); Stanley Mansfield, Sunnyvale, CA (US); Hassan Mostafavi, Los Altos, CA (US)

(73) Assignee: Varian Medical Systems, Technologies, Inc., Palo Alto, CA (US)

( * ) Notice: Subject to any disclaimer, the term of this patent is extended or adjusted under 35 U.S.C. 154(b) by 573 days.

(21) Appl. No.: 09/940,679

(22) Filed: Aug. 27, 2001

(65) Prior Publication Data

US 2002/0023652 A1 Feb. 28, 2002

Related U.S. Application Data (62) Division of application No. 09/178,385, filed on Oct. 23, 1998, now Pat. No. 6,279,579.

(51) Int. Cl.
 *A61B 19/00* (2006.01)
(52) U.S. Cl. .................................................. 128/897
(58) Field of Classification Search ........ 128/897–899; 600/407, 414, 415
See application file for complete search history.

(56) References Cited

U.S. PATENT DOCUMENTS

| | | | |
|---|---|---|---|
| 3,861,807 A | 1/1975 | Lescrenier | 356/152 |
| 3,871,360 A | 3/1975 | Van Horn et al. | |
| 3,952,201 A | 4/1976 | Hounsfield | |
| 4,031,884 A | 6/1977 | Henzel | |
| 4,262,306 A | 4/1981 | Renner | 358/93 |
| 4,463,425 A | 7/1984 | Hirano et al. | 364/417 |
| 4,710,717 A | 12/1987 | Pele et al. | |
| 4,853,771 A | 8/1989 | Witriol et al. | |
| 4,895,160 A | 1/1990 | Reents | |
| 4,971,065 A | 11/1990 | Pearce | |
| 4,994,965 A | 2/1991 | Crawford et al. | |
| 5,080,100 A | 1/1992 | Trotel | 128/653.1 |
| 5,271,055 A | 12/1993 | Hsieh et al. | |

(Continued)

FOREIGN PATENT DOCUMENTS

DE 43 41 324 A1 6/1995

(Continued)

OTHER PUBLICATIONS

Ahlström, K. H. et al. "Pulmonary MR Angiography with Ultrasmall Superparamagnetic Iron Oxide Particles as a Blood Pool Agent and a Navigatior Echo for Respiratory Gating: Pilot Study" *Radiology* (Jun. 1999) 211(3):865-869.

(Continued)

*Primary Examiner*—John P. Lacyk
(74) *Attorney, Agent, or Firm*—Bingham McCutchen LLP (57) ABSTRACT

A system and method for measuring and correcting the position of a patient are disclosed. According to an aspect of the invention, reference coordinates for particular body locations on the patent are determined. At a later treatment session, the relative positioning of the patient's body locations are adjusted to match the relative positioning of the reference coordinates. The entire body of the patient can thereafter be moved as a single unit to match the patient's body location with the absolute location of the reference coordinates.

19 Claims, 7 Drawing Sheets

U.S. PATENT DOCUMENTS

| | | | |
|---|---|---|---|
| 5,279,309 A | 1/1994 | Taylor et al. | 128/782 |
| 5,295,483 A | 3/1994 | Nowacki et al. | 128/660.03 |
| 5,315,630 A | 5/1994 | Sturm et al. | 378/65 |
| 5,389,101 A | 2/1995 | Heilbrun et al. | |
| 5,394,875 A | 3/1995 | Lewis et al. | 128/660.09 |
| 5,446,548 A | 8/1995 | Gerig et al. | 356/375 |
| 5,482,042 A | 1/1996 | Fujita | |
| 5,513,646 A | 5/1996 | Lehrman | |
| 5,538,494 A | 7/1996 | Matsuda | 600/1 |
| 5,565,777 A | 10/1996 | Kanayama et al. | |
| 5,582,182 A | 12/1996 | Hillsman | |
| 5,588,430 A | 12/1996 | Bova et al. | |
| 5,603,318 A | 2/1997 | Heilbrun et al. | |
| 5,619,995 A | 4/1997 | Lobodzinski | |
| 5,622,187 A | 4/1997 | Carol | |
| 5,638,819 A | 6/1997 | Manwaring et al. | |
| 5,662,111 A | 9/1997 | Cosman | 128/653.1 |
| 5,662,112 A | 9/1997 | Heid | |
| 5,727,554 A | 3/1998 | Kalend et al. | 128/653.1 |
| 5,764,723 A | 6/1998 | Weinberger et al. | |
| 5,771,310 A | 6/1998 | Vannah | |
| 5,784,431 A | 7/1998 | Kalend et al. | |
| 5,820,553 A | 10/1998 | Hughes | |
| 5,836,954 A | 11/1998 | Heilbrun et al. | |
| 5,912,656 A | 6/1999 | Tham et al. | |
| 5,954,647 A | 9/1999 | Bova et al. | |
| 5,993,397 A | 11/1999 | Branson | |
| 6,061,644 A * | 5/2000 | Leis | 702/153 |
| 6,076,005 A | 6/2000 | Sontag et al. | |
| 6,144,874 A | 11/2000 | Du | |
| 6,144,875 A | 11/2000 | Schweikard et al. | |
| 6,146,390 A | 11/2000 | Heilbrun et al. | |
| 6,165,181 A | 12/2000 | Heilbrun et al. | |
| 6,185,445 B1 | 2/2001 | Knüttel | |
| 6,185,446 B1 | 2/2001 | Carlsen, Jr. | |
| 6,198,959 B1 | 3/2001 | Wang | |
| 6,272,368 B1 | 8/2001 | Alexandrescu | |
| 6,296,613 B1 | 10/2001 | Emmenegger et al. | |
| 6,300,974 B1 | 10/2001 | Viala et al. | |
| 6,348,058 B1 | 2/2002 | Melkent et al. | |
| 6,370,217 B1 | 4/2002 | Hu et al. | |
| 6,405,072 B1 | 6/2002 | Cosman | |
| 6,434,507 B1 | 8/2002 | Clayton et al. | |
| 6,473,635 B1 | 10/2002 | Rasche | |
| 6,501,981 B1 | 12/2002 | Schweikard et al. | |
| 6,527,443 B1 | 3/2003 | Vilsmeier et al. | |
| 6,611,617 B1 | 8/2003 | Crampton | |
| 6,621,889 B1 | 9/2003 | Mostafavi | |
| 6,665,370 B2 | 12/2003 | Bruder et al. | |
| 6,724,930 B1 | 4/2004 | Kosaka et al. | |
| 2003/0007593 A1 | 1/2003 | Heuscher et al. | |
| 2003/0063292 A1 | 4/2003 | Mostafavi | |
| 2003/0072419 A1 | 4/2003 | Bruder et al. | |
| 2003/0210812 A1 | 11/2003 | Khamene et al. | |
| 2004/0005088 A1 | 1/2004 | Jeung et al. | |
| 2004/0071337 A1 | 4/2004 | Jeung et al. | |
| 2004/0116804 A1 | 6/2004 | Mostafavi | |
| 2004/0218719 A1 | 11/2004 | Brown et al. | |

FOREIGN PATENT DOCUMENTS

| | | |
|---|---|---|
| FI | 79458 | 9/1989 |
| WO | WO98/16151 | 4/1998 |
| WO | WO98/38908 | 9/1998 |

OTHER PUBLICATIONS

Axel, L. et al. "Respiratory Effects in Two-Dimensional Fourier Transform MR Imaging" *Radiology* (Sep. 1986) 160(3):795-801.

Danias, P.G. et al. "Prospective Navigator Correction of Image Position for Coronary MR Angiography" *Radiology* (Jun. 1997) 203:733-736.

Du, Y.P. et al. "A comparison of prospective and retrospective respiratory navigator gating in 3D MR coronary angiography" *Int'l J. Cardiovascular Imaging* (2001) 17:287-294.

Du, Y.P. "Prospective navigator gating with a dual acceptance window technique to reduce respiratory motion artifacts in 3D MR coronary angiography" *Int'l J. Cardiovascular Imaging* (2003) 19:157-162.

Felblinger, J. et al. "Effects of physiologic motion of the human brain upon quantitative $^1$H-MRS: analysis and correction by retrogating" *NMR in Biomedicine* (1998) 11:107-114.

Fishbein, K.W. et al. "The lever-coil: a simple, inexpensive sensor for respiratory and cardiac motion in MRI experiments" *Magnetic Resonance Imaging* (2001) 19:881-889.

Haacke, E.M. and G.W. Lenz "Improving MR Image Quality in the Presence of Motion by Using Rephasing Gradients" *AJR* (Jun. 1987) 148:1251-1258.

Huber, A. et al. "Navigator Echo-Based Respiratory Gating for Three-Dimensional MR Coronary Angiography: Results from Healthy Volunteers and Patients with Proximal Coronary Artery Stenoses" *AJR* (Jul. 1999) 173:95-101.

Lieberman, J.M. et al. "Gated Magnetic Resonance Imaging of the Normal Diseased Heart" *Radiology* (Aug. 1984) 152:465-470.

Manke, D. et al. "Respiratory Motion in Coronary Magnetic Resonance Angiography: A Comparison of Different Motion Models" *J. Magnetic Resonance Imaging* (2002) 15:661-671.

Manke, D. et al. "Model Evaluation and Calibration for Prospective Respiratory Motion Correction in Coronary MR Angiography Based on 3-D Image Registration" *IEEE Transactions on Medical Imaging* (Sep. 2002) 21(9):1132-1141.

McConnell, M.V. et al. "Comparison of Respiratory Suppression Methods and Navigator Locations for MR Coronary Angiography" *AJR* (May 1997) 168:1369-1375.

McConnell, M.V. et al. "Prospective Adaptive Navigator Correction for Breath-Hold MR Coronary Angiography" *MRM* (1997) 37:148-152.

Nikolaou, K. et al. "Navigator Echo-Based Respiratory Gating for Three-Dimensional MR Coronary Angiography: Reduction of Scan Time Using a Slice Interpolation Technique" *J. Computer Assisted Tomography* (2001) 25(3):378-387.

Plein, S. et al. "Three-Dimensional Coronary MR Angiography Performed with Subject-Specific Cardiac Acquisition Windows and Motion-Adapted Respiratory Gating" *AJR* (Feb. 2003) 180:505-512.

Post, J.C. et al. "Three-Dimensional Respiratory-Gated MR Angiography of Coronary Arteries: Comparison with Conventional Coronary Angiography" *AJR* (Jun. 1996) 166:1399-1404.

Regenfus, M. et al. "Comparison of Contrast-Enhanced Breath-Hold and Free-Breathing Respiratory-Gated Imaging in Three-Dimensional Magnetic Resonance Coronary Angiography" *Am. J. Cardiology* (Oct. 1, 2002) 90:725-730.

Schär, M. et al. "The Impact of Spatial Resolution and Respiratory Motion on MR Imaging of Atherosclerotic Plaque" *J. Magnetic Resonance Imaging* (2003) 17:538-544.

Spuentrup, E. et al. "Respiratory motion artifact suppression in diffusion-weighted MR imaging of the spine" *Eur. Radiol.* (2003) 13:330-336.

Thickman, D. et al. "Phase-Encoding Direction upon Magnetic Resonance Image Quality of the Heart" *Magnetic Resonance in Medicine* (1988) 6:390-396.

Wang, Y. et al. "Navigator-Echo-based Real-Time Respiratory Gating and Triggering for Reduction of Respiration Effects in Three-dimensional Coronary MR Angiography" *Radiology* (1996) 198:55-60.

Weber, C. et al. "Correlation of 3D MR coronary angiography with selective coronary angiography: feasibility of the motion adapted gating technique" *Eur. Radiol.* (2002) 12:718-726.

Wiesmann, F. "High-Resolution MRI with Cardiac and Respiratory Gating Allows for Accurate In Vivo Atherosclerotic Plaque Visualization in the Murine Aortic Arch" *Magnetic Resonance in Medicine* (2003) 50:69-74.

Wood, M.L. and R.M. Henkelman "Suppression of respiratory motion artifacts in magnetic resonance imaging" *Med. Phys.* (Nov./Dec. 1996) 13(6):794-805.

Worthley, S.G. et al. "Cardiac gated breath-hold back blood MRI of the coronary artery wall: An in vivo and ex vivo comparison" *Int'l J. Cardiovascular Imaging* (2001) 17:195-201.

Yamashita, Y. et al. "MR Imaging of Focal Lung Lesions: Elimination of Flow and Motion Artifact by Breath-Hold ECG-Gated and Black-Blood Techniques on T2-Weighted Turbo SE and STIR Sequences" *J. Magnetic Resonance Imaging* (1999) 9:691-698.

Josefsson, T. et al. "A Flexible High-Precision Video System for Digital Recording of Motor Acts Through Lightweight Reflex Markers" *Computer Methods & Programs in Biomedicine* (1996) 49:119-129.

Lee, M.W. and I. Cohen "Human Body Tracking with Auxiliary Measurements" *IEEE International Workshop on Analysis and Modeling of Faces and Gestures* (2003) 8 pgs., located at http://iris.usc.edu/-icohen/projects/human/body/index.htm.

Adams, W.B. et al. "Correlator Compensation Requirements for Passive Time-Delay Estimation with Moving Source or Receivers" IEEE (Apr. 1980) ASSP-28(2):158-168.

Balter, J.M. et al. "Uncertainties in CT-Based Radiation Therapy Treatment Planning Associated with Patient Breathing" Int. J. Radiat. Oncol., Biol., Phys. (Aug. 1996) 36:167-174.

Bankman, I.N. et al. "Optimal Detection, Classification, and Superposition Resolution in Neural Waveform Recordings" IEEE (Aug. 1993) 40(8):836-841).

Bellenger, N.G. et al. "Left Ventricular Quantification in Heart Failure by Cardiovasular MR Using Prospective Respiratory Navigator Gating: Comparison with Breath-Hold Acquisition" J. Magn. Reson. Imaging (Apr. 2000) 11:411-417.

Cho, K. et al. "Development of Respiratory Gated Myocardial SPECT System" J. Nucl. Cardiol. (Jan./Feb. 1999) 6:20-28.

Davies, S.C. et al. "Ultrasound Quantitation of Respiratory Organ Motion in the Upper Abdomen" Br. J. Radiol. (Nov. 1994) 67:1096-1102.

Ehman, R.L. et al. Magnetic Resonance Imaging with Respiratory Gating: Techniques and Advantages Am. J. Roentgenol (Dec. 1984) 143:1175-1182.

Fee, M.S. et al. "Automatic Sorting of Multiple Unit Neuronal Signals in the Presence of Anisotropic and non-Gaussian Variability" J. Neuroscience Methods (1996) 69:175-188.

Frölich, H. et al. "A Simple Device for Breath-Level Monitoring During CT" Radiology (Jul. 1985) 156:235.

Hanley, J. et al. "Deep Inspiration Breath-Hold Technique for Lung Tumors: The Potential Value of Target Immobilization and Reduced Lung Density in Dose Escalation" Int. J. Radiat. Oncol., Biol. Phys. (Oct. 1999) 45:603-611.

Henkelman, R.M. et al. "How Important is Breathing in Radiation Therapy of the Thorax?" Int. J. Radiat. Oncol., Biol., Phys. (Nov. 1982) 8:2005-2010.

Hofman, M.B.M. et al. "MRI of Coronary Arteries: 2D Breath-Hold vs. 3D Respiratory-Gated Acquisition" J. of Comp. Assisted Tomography (Jan./Feb. 1995) 19:56-62.

Iwasawa, Tae, et al. "Normal In-Plane Respiratory Motion of the Bilateral Hemidiaphragms Evaluated by Sequentially Subtracted Fast Magnetic Resonance Images" Journal of Thoracic Imaging (1999) 14(2):130-134.

Johnson, L.S. et al. "Initial Clinical Experience with a Video-Based Patient Positioning System" Int. J. Radiat. Oncol., Biol. Phys. (Aug. 1999) 45:205-213.

Kachelriess, Marc, et al. "Electrocardiogram-Correlated Image Reconstruction from Subsecond Spiral Computed Tomography Scans of the Heart" Med. Phys. (Dec. 1998) 25(12):2417-2431.

Keatley, Eric, et al. "Computer Automated Diaphragm Motion Quantification in a Fluoroscopic Movie" Dept. of Medical Physics, Memorial Sloan-Kettering Cancer Center, New York; 3 pgs.

Kim, W.S., et al. "Extraction of Cardiac and Respiratory Motion Cycles by Use of Projection Data and its Applications to NMR Imaging" Magnetic Resonance in Medicine (1990) 13:25-37.

Korin, H.W. et al. "Respiratory Kinematics of the Upper Abdominal Organs: A Quantitative Study" Magn. Reson. Med. (Jan. 1992) 23:172-178.

Kubo, Hideo D., et al. "Respiration Gated Radiotherapy Treatment: A Technical Study" Phys. Med. Biol. (1996) 41:83-91.

Kubo, H. Dale et al. "Potential and Role of a Prototype Amorphous Silicon Array Electronic Portal Imaging Device in Breathing Synchronized Radiotherapy" Med. Phys. (Nov. 1999) 26(11):2410-2414.

Kubo, H. Dale, et al. "Breathing-Synchronized Radiotherapy Program at the University of California Davis Cancer Center" Med. Phys. (Feb. 2000) 27(2):346-353.

Kubo, H.D. et al. "Compatibility of Varian 2100C Gated Operations with Enhanced Dynamic Wedge and IMRT Dose Delivery" Med. Phys. (Aug. 2000) 27:1732-1738.

Kutcher, G.J. et al. "Control, Correction, and Modeling of Setup Errors and Organ Motion" Semin. Radiat. Oncol. (Apr. 1995) 5:134-145.

Lethimonnier, F. et al. "Three-Dimensional Coronary Artery MR Imaging Using Prospective Real-Time Respiratory Navigator and Linear Phase Shift Processing: Comparison with Conventional Coronary Angiography" Magn. Reson. Imaging (1999) 17:1111-1120.

Lewis, C.E. et al. "Comparison of Respiratory Triggering and Gating Techniques for the Removal of Respiratory Artifacts in MR Imaging" Radiology (Sep. 1986) 160:803-810.

Li, Debiao, et al. "Coronary Arteries: Three-Dimensional MR Imaging with Retrospective Respiratory Gating" Radiology (Dec. 1996) 201(3):857-863.

Luker, Gary D., et al. "Ghosting of Pulmonary Nodules with Respiratory Motion: Comparison of Helical and Conventional CT Using an In Vitro Pediatric Model" AJR (Nov. 1996) 167:1189-1193.

Mageras, G.S. et al. "Respiratory Motion-Induced Treatment Uncertainties" Patras Medical Physics 99—VI International Conference On Medical Physics, Monduzzi Editore (Sep. 1999) pp. 33-39.

Mageras, G.S. "Interventional Strategies for Reducing Respiratory-Induced Motion in External Beam Therapy" The Use of Computers In Radiation Therapy XIIIth International Conference, Heidelberg, Germany (May 2000) pp. 514-516.

Mageras, G. et al. "Initial Clinical Evaluation of a Respiratory Gating Radiotherapy System" in 22nd Annual EMBS International Conference Chicago, IL (Jul. 23-28, 2000) pp. 2124-2127.

Mah, Katherine, et al. "Time Varying Dose Due to Respiratory Motion During Radiation Therapy of the Thorax"; Proceedings of the Eighth Int'l Conference on the Use of Computers In Radiation Therapy Toronto, Canada (Jul. 9-12, 1984) pp. 294-298.

Mah, D. et al. "Technical Aspects of the Deep Inspiration Breath Hold Technique in the Treatment of Thoracic Cancer" Int. J. Radiat. Oncol., Biol., Phys. (Nov. 2000) 48:1175-1185.

Malone, S. et al. "Respiratory-Induced Prostate Motion: Quantification and Characterization" Int. J. Radiat. Oncol., Biol., Phys. (Aug. 2000) 48:105-109.

Moerland, M.A. et al. "The Influence of Respiration Induced Motion of the Kidneys on the Accuracy of Radiotherapy Treatment Planning, a Magnetic Resonance Imaging Study" Radiotherapy Oncol. (1994) 30:150-154.

Mori, Masayuki, et al. "Accurate Contiguous Sections Without Breath-Holding on Chest CT: Value of Respiratory Gating and Ultrafast CT" AJR (May 1994) 162:057-1062.

Nevatia, R. et al. "Human Body Tracking with Articulated Human Body Model" (Nov. 2002) pp. 1-3.

Ohara, K. et al. "Irradiation Synchronized with Respiration Gate" Int. J. Radiat. Oncol., Biol. Phys. (Oct. 1989) 17:853-857.

Oshinski, J.N. et al. "Two-Dimensional Coronary MR Angiography Without Breath Holding" Radiology (Dec. 1996) 201:737-743.

Paradis, A.L. et al. "Detection of Periodic Signals in Brain Echo-Planar Functional Images" IEEE (Jan. 1, 1997) pp. 696-697.

Peltola, Seppo M.Se. "Gated Radiotherapy to Compensate for Patient Breathing"; Proceedings of the Eleventh Varian Users Meeting; Marco Island, Florida; May 11-13, 1986.

Ramsey, C.R. et al. "A Comparison of Beam Characteristics for Gated and Nongated Clinical X-Ray Beams" Med. Phys. (Oct. 1999) 26:2086-2091.

Ramsey, C.R. et al. "Clinical Efficacy of Respiratory Gated Conformal Radiation Therapy" Medical Dosimetry (1999) 24:115-119.

Ritchie, Cameron J., et al. "Predictive Respiratory Gating: A New Method to Reduce Artifacts on CT Scans" Radiology (Mar. 1994) 190(3):847-852.

Robinson, Terry E., et al. "Standardized High-Resolution CT of the Lung Using a Spirometer-Triggered Electron Beam CT Scanner" AJR (Jun. 1999) 172:1636-1638.

Rogus, R.D. et al. "Accuracy of a Photogrammetry-Based Patient Positioning and Monitoring System for Radiation Therapy" Med. Phys (May 1999) 26:721-728.

Rosenzweig, K.E. et al. "The Deep Inspiration Breath Hold Technique in the Treatment of Inoperable Non-Small Cell Lung Cancer" Int. J. Radiat. Oncol., Biol., Phys. (Aug. 2000) 48:81-87.

Ross, C.S. et al. "Analysis of Movement of Intrathoracic Neoplasms Using Ultrafast Computerized Tomography" Int. J. Radiat. Oncol., Biol., Phys. (Mar. 1990) 18:671-677.

Runge, V.M. et al. "Respiratory Gating in Magnetic Resonance Imaging at 0.5 Tesla" Radiology (May 1984) 151:521-523.

Sachs, T.S. et al. "Real-Time Motion Detection in Spiral MRI Using Navigators" Magn. Reson. Med. (Nov. 1994) 32:639-645.

Schwartz, L.H. et al. "Kidney Mobility During Respiration" Radiother. Oncol. (1994) 32:84-86.

Shirato, H. et al. "Four-Dimensional Treatment Planning and Fluroscopic Real-Time Tumor Tracking Radiotherapy for Moving Rumor" Int. J. Radiat. Oncol., Biol., Phys. (Sep. 2000) 48:435-442.

Sinkus, Ralph, et al. "Motion Pattern Adapted Real-Time Respiratory Gating" Magnetic Resonance in Medicine (1999) 41:148-155.

Solberg, Timothy D., et al. "Feasibility of Gated IMRT" 3 pgs.

Suramo, M.P. et al. "Cranio-Caudal Movements of the Liver, Pancreas and Kidneys on Respiration" Acta Radiol. Diagn. (1984) 2:129-131.

Tada, Takuhito, et al. "Lung Cancer: Intermittent Irradiation Synchronized with Respiratory Motion-Results of a Pilot Study" Radiology (Jun. 1998) 207(3):779-783.

van Geuns, R.J. et al. "Magnetic Resonance Imaging of the Coronary Arteries: Clinical Results from Three Dimensional Evaluation of a Respiratory Gated Technique" Heart (Oct. 1999) 82:515-519.

Wang, Yi, et al. "Implications for the Spatial Resolution in Coronary Imaging" Magnetic Resonance in Medicine (1995) 33:713-719.

Weiger, Markus, et al. "Motion-Adapted Gating Based on k-Space Weighting for Reduction of Respiratory Motion Artifacts" Magnetic Resonance in Medicine (1997) 38:322-333.

Wong, John W., et al. "The Use of Active Breathing Control (ABC) to Reduce Margin for Breathing Motion" Int. J. Radiation Oncology Biol. Phys. (Jul. 1999) 44(4):911-919.

Woodard, Pamela K., et al. "Detection of Coronary Stenoses on Source and Projection Images Using Three-Dimensional MR Angiography with Retrospective Respiratory Gating: Preliminary Experience" AJR (Apr. 1998) 170(4):883-888.

Yorke, Ellen et al. "Respiratory Gating of Sliding Window IMRT" in 22nd Annual EMBS International Conference Chicago, IL (Jul. 23-28, 2000) pp. 2118-2121.

Yuan, Q. et al. "Cardiac-Respiratory Gating Method for Magnetic Resonance Imaging of the Heart" Magn. Reson. Med. (Feb. 2000) 43:314-318.

Ference A. Jolesz; "Image-Guided Procedures and the Operating Room of the Future"; Radiology, SPL Technical Report # 48; May 1997; 204; 601-612.

Preliminary Sales Brochure entitled "Kinematic Measurement Systems" by Qualisys printed Apr. 4, 1994.

Gerig et al.; "The Development and Clinical Application Of A Patient Position Monitoring System" published in *SPIE*; vol. 2350; Videometrics III (1994); pp. 59-72.

Baroni, Guido et al.; "Real-Time Motion Analysis For Definition And Control Of Patient Position In Radiotherapy" ; published in *SPIE* in 1996; vol. 2709; pp. 506-515.

Kubo, Hideo D., et al.; "Respiration Gated Radiotherapy Treatment: A Technical Study"; *Phys. Med. Biol.*; Jan. 1996; Bristol, Great Britain; No. 1, pp. 83-91.

Preliminary Search Brochure entitle "Kinematic Measurement Systems" by Qualisys printed Apr. 4, 1994.

Gerig et al, "The Development and Clinical Application of a Patient Position Monitoring System" publish in SPIE, vol. 2350, Videometrics III (1994) pp. 59-72.

Baroni, Guido and Ferrigno, Giancarlo, "Real-time motion analysis for definition and control of patient position in radiotherapy", publish in SPIE in 1996, vol. 2709, pp. 506-515.

Lopresti, B. J., et al, "Implementation and Performance of an Optical Motion Tracking System for High Resolution Brain PET Imaging", IEEE Transaction on Nuclear Science, vol. 46, No. 6, Dec. 1999, pp. 2059-2067.

\* cited by examiner

MARKERS AND SYSTEMS FOR DETECTING SUCH MARKERS

This application is a divisional application of Ser. No. 09/178,385, filed Oct. 23, 1998, which will issue as U.S. Pat. No. 6,279,579 on Aug. 28, 2001.

BACKGROUND OF THE INVENTION

1. Field of the Invention

The present invention relates to medical methods and systems. More particularly, the invention relates to a method and system for positioning patients that undergo medical treatment procedures.

2. The Related Art

The accurate placement and positioning of patients is crucial when performing many types of medical treatments. One category of medical treatments in which the proper placement and verification of the position of patients/patient body parts is of particular importance is in the field of radiation therapy.

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. To minimize damage to surrounding body tissues, many conventional treatment methods utilize "dose fractionating" to deliver the radiation dosage in a planned series of treatment sessions that each delivers only a portion of the total planned dosage. Healthy body tissues typically have greater capacity to recover from the damage caused by exposed radiation. Spreading the delivered radiation over many treatment sessions allows the healthy tissue an opportunity to recover from radiation damage, thus reducing the amount of permanent damage to healthy tissues while maintaining enough radiation exposure to destroy tumoral tissue.

The efficacy of the radiation treatment depends in large part upon the ability to irradiate the exact same position on the body at the various radiation sessions. The goal is to place the patient in the same position relative to the radiation source at each and every treatment session. Inaccuracies in positioning the patient could result in errors in radiation dosage and/or treatment locations, leading to unpredictable disease relapse or damage to healthy tissues. Maintaining the linear accelerator/radiation source in a precise and repeatable position does not normally present a problem. The problem arises when attempting to recreate the same body position by the patient at every radiation session. In conventional medical treatment systems, the accurate placement and verification of a repeating treatment location on the human body remains a significant problem in implementing dose fractionating treatment plans.

One approach to controlling patient positioning is to place marks or tattoos at specific locations on the patient's skin. Several laser or light sources from predetermined locations project beams of light at the patient's body. To control the patient positioning, a therapist shifts the position of the patient until the marks are aligned with the lines of light from the lasers or light sources. A significant drawback to this approach is that the accuracy and consistency of the patient positioning is heavily dependent upon the skill level of the therapist in manually positioning the patient. In addition, with heavier patients, it is possible that only the skin of the patient is moved into the proper position without moving the body part to be irradiated into the appropriate position. Moreover, this approach does not provide an efficient way to record and reflect the positioning quality in the patient's records.

Another approach to controlling patient positioning is to utilize an immobilization device to maneuver the patient into a particular position. An immobilization device physically attaches to the human body to keep the patient from moving once proper positioning is achieved. A drawback to using an immobilization device is that such devices to not exist for all body parts. Immobilization devices are generally effective only for positioning the head and neck of a patient. Moreover, in many known immobilization devices, a patient can still move to a significant degree within the confines of the immobilization device. In addition, these devices can be extremely uncomfortable for the patient.

Positioning a patient with video cameras has been applied to stereotactic radiosurgery of the brain where the patient's skull is positioned as a rigid object. However, there are drawbacks to applying known positioning techniques using video cameras to non-rigid portions of the body. For example, such implementations have been incapable of effectively guiding the therapist through the steps to be taken for achieving proper posture and position. Therefore, therapist confusion occurs resulting in a lengthy positioning process.

Thus, there is a need for a system and method to address the above-described problems of the related art. There is a need for a method and system that can accurately and consistently control the position of a patient for medical treatment.

SUMMARY OF THE INVENTION

The present invention provides a method and system for measuring the position of a patient, as well as a method and system for positioning a patient for medical treatment procedures.

According to an aspect of the invention, reference coordinates for particular body locations on the patient are determined. At a later treatment session, the relative positioning of the patient's body locations are adjusted to match the relative positioning of the reference coordinates. The entire body of the patient can thereafter be moved as a single unit to match the absolute position of the reference coordinates.

Further details of aspects, objects, and advantages of the invention are described below in the detailed description, drawings, and claims.

BRIEF DESCRIPTION OF THE DRAWINGS

The accompanying drawings are included to provide a further understanding of the invention and, together with the Detailed Description of Embodiment(s), serve to explain the principles of the invention.

FIG. 6b is a front view of the camera of FIG. 6a.

FIG. 7b is a perspective view of the retro-reflective marker of FIG. 7a.

DETAILED DESCRIPTION OF EMBODIMENT(S)

Process Overview

Figure 1:
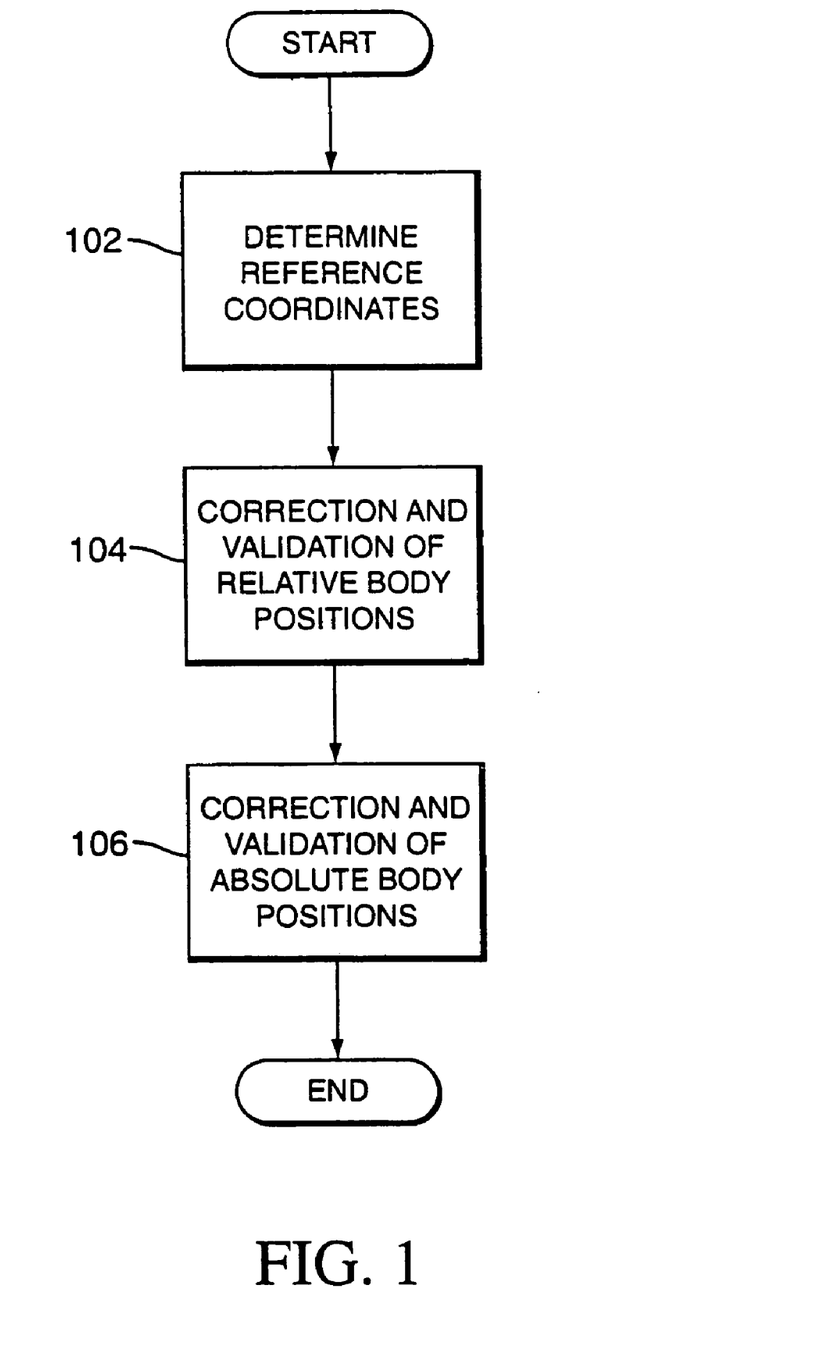
FIG. 1 is a process flowchart showing the high level actions performed in one embodiment of the invention.

FIG. 1 is a process flowchart showing the high level actions performed in an embodiment of the present invention. The method of the present invention begins with the measurement and storage of reference coordinates for various body locations on a patient's body (102). Prior to delivery of radiation treatment at each treatment session, the patient should be positioned such that the actual coordinates of these locations on the patient's body match the reference coordinates. Assuming the radiation source is placed in its original position, this will ensure that the patient consistently and repeatably receives treatment in the same location at every session.

When undergoing treatment at the various treatment sessions, the patient is preferably placed upon a treatment table, treatment couch, or other type of patient support structure. For purposes of explanation, the term "treatment table" shall be used in this document to refer any support structure that can be used to support a patient. Initially, the patient is likely be in an incorrect position relative to the reference coordinates. Consistent with the invention, the initial positioning action involves the correction of the patient's "posture" (104). Posture refers the position of one or more of a patient's body parts relative to that patient's other body parts. In process action 104, the measured body locations on the patient's body are repositioned such that the relative positioning of the patient's body parts match the relative positioning of the reference coordinates. To achieve this goal, the positioning system provides specific instructions to correct the relative positioning of the patient's body parts.

Once the patient's posture has been corrected, the measured body locations should be in the correct positions with respect to the rest of the patient's body. However, the absolute coordinates of the patient's body positions may be incorrect. If the patient is in the correct posture, then all of the patient's body locations will be misaligned by the exact same offset parameter values when compared to the reference coordinates. Thus, the patient's entire body can be shifted as a single unit to place the patient in the correct absolute coordinates that match the reference coordinates (106).

The combination of the actions to correct and validate relative position errors (104) and absolute position errors (106) greatly accelerates the time needed for patient setup prior to a treatment session. Moreover, the present invention allows more precise recordation and verification of patient positioning in real-time during the treatment sessions.

In an alternate embodiment, after the relative and absolute positioning actions have been performed, an additional positioning action can be performed with respect to the patient's internal organs. This additional positioning action is performed to adjust the internal target volume instead of the patient's external features, and can be used to precisely position the patient's internal organs for treatment. Each of the above process actions will be explained in more detail below.

Method and System of the Invention

In an embodiment, the body locations chosen for measuring reference coordinates fall within two general categories. First, one or more body location(s) can be chosen for measurement in the general vicinity of the body structure/organ undergoing treatment. Second, other body location(s) can be chosen if movement of those other body locations affect the orientation or location of the body structure/organ undergoing treatment. For example, a patient undergoing treatment in the breast area will preferably have one or more reference positions measured in the chest area, and possibly in other areas of the body that can affect the position of the breast area, such as the upper arm and neck areas. A patient undergoing treatment in the prostate area will preferably have one or more reference positions measured in the hip area, and possibly in other areas of the body that can affect the movement of the prostate area, such as the upper leg areas.

Figure 2:
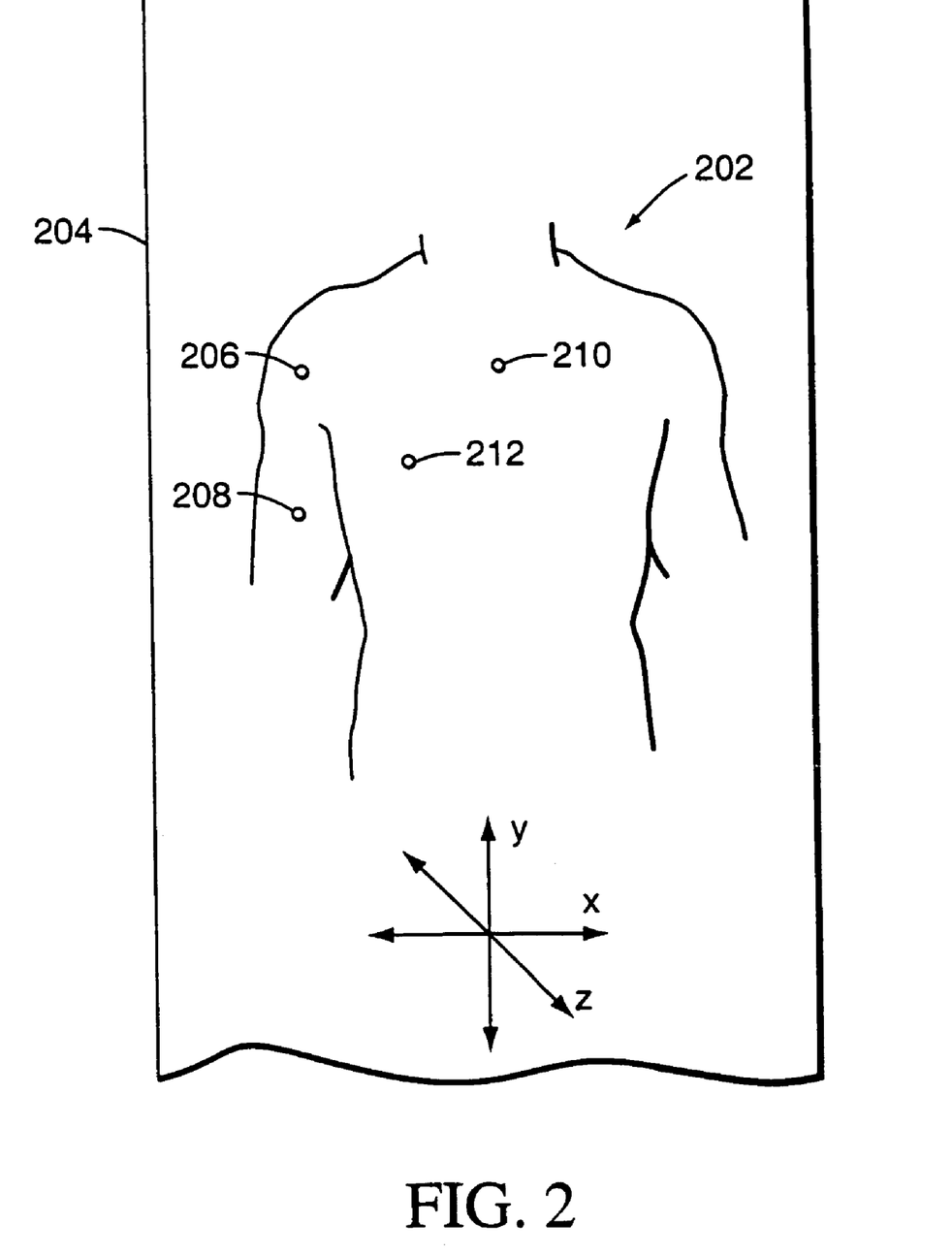
FIG. 2 depicts a plurality of reference body locations located on a patient's body.

Shown in FIG. 2 are the upper torso and upper arms of a patient 202 resting on a treatment table 204. For the purposes of illustration, a plurality of body locations 206, 208, 210, and 212 has been marked on patient 202. Each of the body positions 206, 208, orientation/location of a body organ undergoing treatment. Prior to the initial treatment session, each of these body locations are measured to provide reference coordinates in Cartesian space. In an embodiment, the isocenter of the system is presumed to be located at coordinate (0,0,0). All measured body positions are given coordinates relative to the isocenter. For purposes of explanation, the orientation of the x, y, and z-axes are as shown in FIG. 1. Other orientation methodologies can be employed within the scope of the invention. For example, in an alternate embodiment, the orientation of the x, y, and z-axes can be defined with reference to the axial movement or rotation of a gantry holding the radiation source or linear accelerator.

Table 1 provides examples of reference coordinates that may be measured for body locations 206, 208, 210, and 212:

TABLE 1

| Body Location | Reference Coordinate |
| --- | --- |
| Body location 206 | (−18, 10, −5) |
| Body location 208 | (−20, −5, −10) |
| Body location 210 | (0, 10, 2) |
| Body location 212 | (−10, 0, 4) |

Figure 3A:
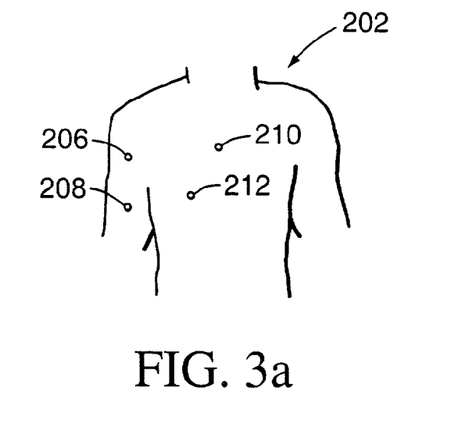
FIGS. 3a–e illustrate the application of an embodiment of the invention to correct a patient's relative and absolute positions.

Referring to FIGS. 3a, 3b, 3c, and 3d, these figures illustrate the positioning process of the present invention. The patient 202 and marked body locations 206, 208, 210, and 212 of FIG. 2 has been duplicated in FIG. 3a. Thus, FIG. 3a represents the reference position for patient 202. It is assumed that the reference coordinates for body locations 206, 208, 210, and 212 in FIG. 3a are as set forth in Table 1.

Figure 3B:
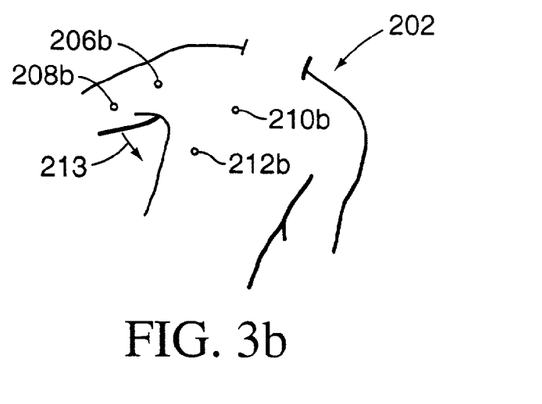

FIG. 3b illustrates an example of an initial position and posture of the patient 202 prior to the beginning of a treatment session. Note that in FIG. 3b, the patient's posture is different than the reference posture of the patient 202 as shown in FIG. 3a. In other words, the relative positions between body locations 206b, 208b, 210b, and 212b shown in FIG. 3b are different than the relative positions between their corresponding reference body locations 206, 208, 210, and 212 in FIG. 3a. In particular, the patient's arm and shoulder (body locations 206b and 208b) are in the wrong position relative to the rest of the patient's body. Furthermore, the absolute position and/or orientation of the patient's body are incorrect. Specifically, the patient 202 in FIG. 3b has rotationally deviated from the proper reference position shown in FIG. 3a.

To correct the patient's posture, specific measured body locations on the patient are repositioned such that they are in the correct positions relative to other measured body locations.

The reference coordinate for body location 206 in FIG. 3a is (−18, 10, 5) and the reference coordinate for body location 208 is (−20, −5, −10). This means that the offset between the reference coordinate for body location 206 and reference coordinate for body location 208 can be expressed with respect to each of the Cartesian axes as follows:

x-axis: −2, y-axis: −15, z-axis: −15

In an embodiment, the x-axis offset between the two body locations is calculated by subtracting the x-coordinate for body location 206 from the x-coordinate for body location 208. Similarly, the y-axis offset between the two body locations is calculated by subtracting the y-coordinate for body location 206 from the y-coordinate for body location 208. The z-axis offset between the two body locations is calculated by subtracting the z-coordinate for body location 206 from the z-coordinate for body location 208.

To correct relative positioning errors between body location 206b and 208b, the relative offset between these two body locations should be manipulated to match the offset measured for their corresponding reference coordinates. For example, if patient 202 in FIG. 3b has been incorrectly positioned such that body location 206b is moved to coordinate (0,0,0), then body location 208b can be moved to coordinate (−2, −15, −15) to re-establish the same relative positioning between these two body locations as was established for their corresponding reference coordinates. The same relative positioning can be obtained by moving body location 206b instead of body location 208b, so long as the offset between the two body locations is corrected to the reference offset. Alternatively, both body locations can be moved during this process, as long as the end result is that the relative offset between these two body locations matches the relative offset of the corresponding reference coordinates.

Similarly, the offset between the reference coordinate for body location 210 (0, 10, 2) and reference coordinate for body location 212 (−10, 0, 4) can be expressed as: x axis: −10, y axis: −10, z axis: −2

Thus, if body location 210b in FIG. 3b is moved to coordinate (0,0,0), then body location 212b can be moved to coordinate (−10, −10, −2) to maintain the same relative positioning that was measured and established between their corresponding reference coordinates.

The offset between the reference coordinate for body location 208 (−20, −5, −10) and body location 210 (0, 10, 2) can be expressed as:

x axis: 20, y axis: 15, z axis: 12

If the body location 208b in FIG. 3b is moved to coordinate (0,0,0), then body location 210b can be moved to coordinates (20, 15, 12) to maintain the same relative positioning that was measured and established between their corresponding reference coordinates.

In an embodiment, the positioning system provides specific instructions to correct the positioning of the patient's body parts. There are a number of techniques to provide a positioning plan or recipe to correct the patient's posture. In one approach, the collection of marked body locations is mathematically translated as a rigid object to overlap with the collection of reference positions. In other words, the location data for the entire collection of marked body locations is mathematically overlaid atop the location data for the collection of reference positions. Thereafter, the location data for the entire collection of marked body locations is logically shifted as a single unit to attempt to find a best overall match between the collection of marked body locations and the collection of reference positions. This can be done by either a center of mass translation, or by matching as many marked body locations to reference locations as possible. The remaining residual error between the position of each unmatched marked body location and its corresponding reference location define the posture error associates with that body location. In this way, the system can provide specific instructions that precisely guide on how to move each body part in order to correct posture errors to an accepted level. These specific instructions can be used by a therapist to make the posture corrections.

To illustrate, consider the collection of marked body locations 206b, 208b, 210b, and 212b in FIG. 3b. If the entire collection of marked body location in FIG. 3b is mathematically translated as a rigid object to overlap with the collection of reference locations in FIG. 3a, then the point of best match could be where body location 210b lines up with reference location 210 and body location 212b lines up with reference location 212. The alignment errors between the relative locations of body locations 206b and 208b and reference locations 206 and 208 would then define the posture errors.

In a display image, the positioning system can present visual instructions to correct the posture errors. Instruction arrow 213 in FIG. 3b is an example of a visual instruction that can be presented to a therapist to provide specific pictorial guidance to correct posture errors. The instruction arrow 213 can be overlaid or ghosted over the image of the patient to facilitate the correction of the posture error. FIG. 3e depicts a magnified view of the instruction arrow 213 from FIG. 3b. As indicated, instruction arrow 213 provides specific guidance as to the direction of correction, as well as the magnitude of correction required.

In an alternate embodiment, posture correction is accomplished by selecting a single measured body location as the primary reference point. Each other measured body location is positioned such that its position relative to the primary reference point matches the relative offset established and measured between the same two points for the reference coordinates. Alternatively, posture correction can be accomplished in a chained approach, in which a first measured body location is re-positioned relative to a second measured body location. Once the first and second measured body locations have been properly positioned relative to each other, a third measured body location is positioned relative to the second measured body location. Once the second and third measured body locations have been properly positioned relative to each other, a fourth measured body location is positioned relative to the third measured body location. This continues until all the remaining measured body locations have been properly positioned.

Figure 3C:
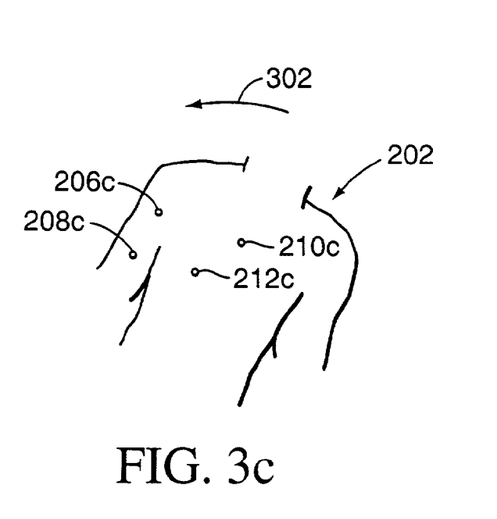

FIG. 3c depicts patient 202 once the posture errors of FIG. 3b have been corrected. It can be appreciated that once the posture of the patient has been corrected, the relative offsets for all the measured body locations will match the relative offsets measured and established for their corresponding reference coordinates. Thus, the relative positioning between body locations 206c, 208c, 210c, and 212c in FIG. 3c match the relative positioning between the reference coordinates for body locations 206, 208, 210, and 212 in FIG. 3a. In particular, the upper arms and shoulder of the patient 202 (body locations 206c and 208c) have been repositioned to the same position relative to the rest of the body as was measured and established for the reference coordinates.

Once posture correction and verification has been performed, the absolute position of the patient's body must be corrected and/or verified. Even if posture errors have been corrected, it is possible that the coordinates of the measured body locations may not match the absolute coordinates of the reference coordinates. In the example of FIG. 3c, although the patient's posture has been corrected, the absolute position of the patient 202 is not correct since the patient's body is rotationally shifted from the reference position shown in FIG. 3a. However, since posture corrections have already been performed, every part of the patient's body should be misaligned by the exact same offset parameters. Thus, rather than having to maneuver individual parts of the patient to establish proper positioning, the patient's entire body can be maneuvered as a unit into the proper position to match the absolute position of the reference coordinates.

Figure 3D:
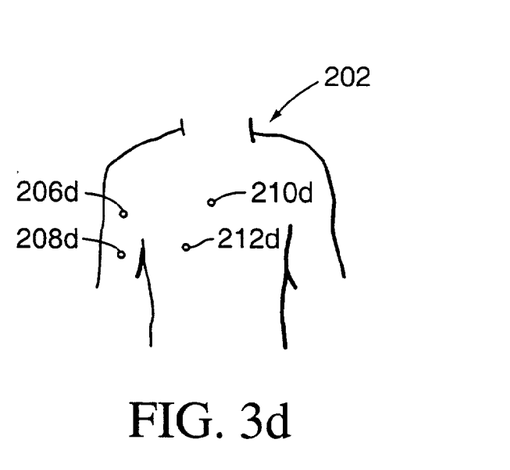
Figure 3E:
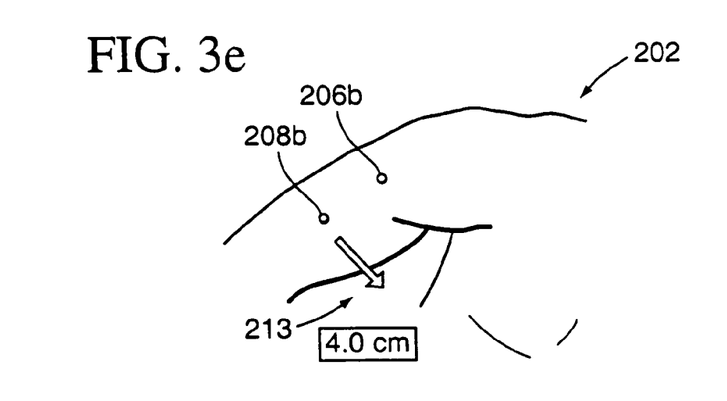

In the example of FIG. 3c, the patient's entire body is rotated in the directed indicated by arrow 302. In an embodiment, this movement of the patient's entire body is effected by moving the position of the support structure that the patient is resting on, e.g., the treatment table. FIG. 3d depicts patient 202 once the patient's entire body has been repositioned. In FIG. 3d, the absolute coordinates of body locations 206d, 208d, 210d, and 212d have been positioned match their corresponding reference coordinates.

According to an embodiment, an additional positioning action can be performed with respect to the internal treatment area of the patient. In certain circumstances, the internal body structure or organ to be treated may shift from a previous location/position, even though the external body locations have been placed to match the reference coordinates.

A first method to perform internal positioning measurements and corrections comprises the use of an imaging system, such as an x-ray imaging system, that can detect specific internal landmarks within the patient's body. Such landmarks can include particular bony structures near the organ to be treated. The imaging system is used to measure reference locations for the bony structures chosen as landmarks. At a following treatment session, the imaging system is used to measure the positions of the same landmark structures within the patient. The patient undergoes fine body adjustments until the landmark structures are positioned at the previously measured reference locations.

A second method to perform internal positioning measurements and corrections comprises the use of an imaging system that can directly image the organ or body structure undergoing treatment, such as ultrasound or MRI imaging systems. The imaging system measures a reference position and orientation for the organ or body structure undergoing treatment. For example, if an ultrasound imaging system is used, then the system can detect the position of an organ or body structure with respect to the ultrasound probe. The exact position of the ultrasound probe is measured with respect to the rest of the system. One or more markers (described in more detail below) can be affixed to the ultrasound probe to determine its position. Based upon the position of the ultrasound probe, the position of the internal organ or body structure can be calculated relative to the rest of the system. At a following treatment session, the patient undergoes fine body adjustments to place the organ or body structure into the original reference position and orientation.

Figure 4:
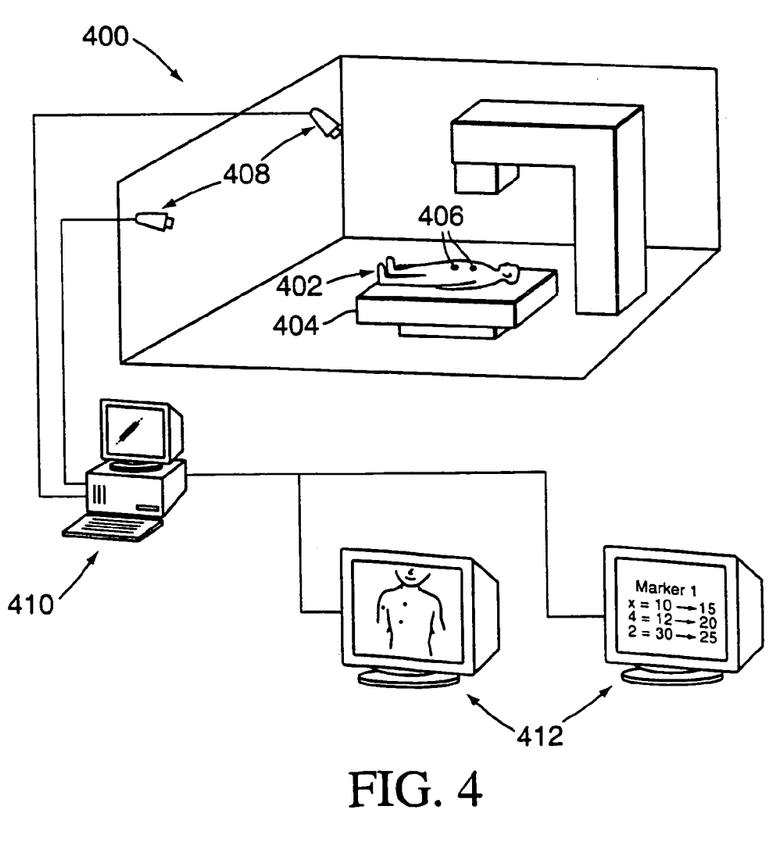
FIG. 4 depicts a system for measuring and correcting a patient's position according to an embodiment of the invention.

FIG. 4 depicts a patient measuring and positioning system 400 according to an embodiment of the present invention. Shown in FIG. 4 is a patient 402 supported by a treatment table 404. A plurality of markers 406 (preferably retro-reflective or reflective markers) are affixed to a plurality of body locations on the patient 402. A method to select particular body locations upon which to affix retro-reflective markers 406 has been described above. In an embodiment, each retro-reflective marker 406 is comprised of reflective material that can reflect light, whether in the visible or invisible wavelengths. Two or more cameras 408 are positioned to detect and receive light that reflect from markers 406. The output of cameras 408 are sent to a computer 410 or other type of processing unit having the capability to receive video images. According to a particular embodiment, computer 410 comprises an Intel Pentium-based processor running Microsoft Windows NT and includes a video frame grabber card that is a multi-channel device, having a separate channel for each camera 408 utilized in the system.

In operation, one or more illumination sources (which are infrared sources in the preferred embodiment) project light at the patient 402 on treatment table 404. The generated light is reflected from retro-reflective markers 406, thereby indicating the position of these retro-reflective markers 406. The cameras 408, which are directed at patient 402, capture and detect the reflected light from the retro-reflective markers 406. Each camera 408 generates video images that show the position of the retro-reflective markers 406 within its video frame. The generated video images are sent to computer 410 for further processing.

Computer 410 receives video images from cameras 408. In general, the received video images from each camera 408 only show the position of the retro-reflective markers 406 relative to the particular camera 408 that produces the image. The two sets of images received from each camera 408 are used by computer 410 to triangulate the absolute coordinates of each retro-reflective marker 406. At the first treatment session, the reference coordinates for each retro-reflective marker 406 are measured and stored at the computer 410. Thereafter, at each additional treatment session, the system 400 can measure in real-time the absolute coordinates of each retro-reflective marker 406 and compare the real-time coordinates of the markers 406 to the stored reference coordinates. Although only two cameras 408 are shown in FIG. 4, any number of cameras 408 may be employed in system 400 to receive video images of the patient 402 and retro-reflective markers 406. Information regarding the location and orientation of each camera 408 is provided to computer 410 to facilitate the triangulation computations.

A possible inefficiency in tracking the retro-reflective markers 406 is that the markers may appear anywhere on the video frame, and all of the image elements of the video frame may have to be examined to determine the location of the retro-reflective markers 406. Thus, in an embodiment, the initial determination of locations for the retro-reflective markers 406 involves an examination of all of the image elements in the video frame. If the video frame comprise 640 by 480 image elements, then all 307200 (640*480) image elements are initially examined to find the location of the markers 406.

For real-time tracking of the retro-reflective markers 406, examining every image element for every video frame to determine the location of the markers 406 in real-time could consume a significant amount of system resources. Thus, in an embodiment, the real-time tracking of the retro-reflective markers 406 can be facilitated by processing a small region of the video frame, referred to herein as "tracking gate", that is placed based on estimation of the locations of the already-identified markers 406 in the video frame. The previously determined location of a marker 406 is used to define an initial search range (i.e., the tracking gate) for that same marker in real-time. The tracking gate is a relatively small portion of the video frame that is centered at the previous location of the marker 406. The tracking gate is expanded only if it does not contain the new location of the marker 406. As an example, consider the situation when the previously determined location of a particular marker is image element (50,50) in a video frame. If the tracking gate is limited to a 50 by 50 area of the video frame, then the tracking gate for this example would comprise the image elements bound within the area defined by the coordinates (25,50), (75,50), (50,25), and (50,75). The other portions of the video frame are searched only if the marker 406 is not found within this tracking gate.

At each treatment session, the retro-reflective markers 406 are affixed to the same pre-determined positions on the body of patient 402. At the beginning of each treatment session, the coordinates for each retro-reflective marker 406 are triangulated by computer 410. If the relative or absolute positioning of the retro-reflective markers 406 are incorrect, then the computer produces specific information that can be used to correct these errors. This real-time feedback regarding the position of the retro-reflective markers 406 can be provided throughout the treatment sessions so that any position errors that arise during treatment can be detected and corrected.

In an embodiment, posture correction is performed manually by a therapist or attendant. Computer 410 provides instructions on a video display device 412 regarding the specific movement of the measured body location that can be used to establish the proper relative positioning of the patient's body. For example, video display device 412 may display information regarding the exact x, y, and z-axis adjustments needed to particular body locations to correct posture errors. Alternatively, the treatment table 404 may comprise body manipulation fixtures that are controlled by computer 410. In this embodiment, the computer-controlled fixtures are moved by the computer 410 to automatically adjust the posture of patient 402 to establish the proper relative positioning of the various body locations.

Once the proper posture is established, the patient 402 is shifted into the proper absolute position. In an embodiment, the treatment table 404 comprises a moveable structure that can be positionally and rotationally adjusted. The entire body of the patient 402 is shifted as a single unit by the treatment table 404 to establish the proper absolute coordinates to exactly match the reference coordinates. In the preferred embodiment, the movement of treatment table 404 is controlled by the computer 410. Once posture adjustments are made, the computer 410 directs the movement of the treatment table 404 to bring patient 402 into the proper absolute position. In an alternate embodiment, the treatment table 404 is manually maneuvered by an attendant or therapist to place the patient 402 in the correct absolute position.

A video display device 412 provides information regarding the proper movement of the treatment table 404 to effect the position correction. Fine adjustments to the patient's position to correct position errors of internal organs or body structures can also be performed by moving the treatment table 404. In an embodiment, the movement is controlled by computer 410.

Figure 5:
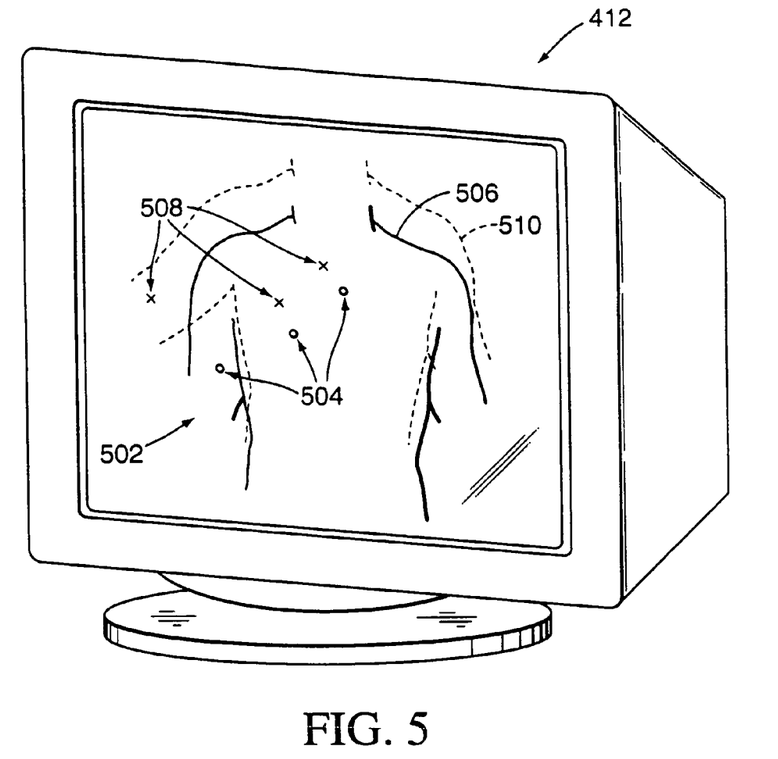
FIG. 5 illustrates a video display device and an example of a video image.

Referring to FIG. 5, an embodiment of system 400 provides a video image 502 of the patient (or particular body locations on the patient) on a video display device 412. The video image is provided to assist a therapist or attendant in positioning the patient. Within the video image 502, the reference positions of the retro-reflective markers are displayed as illuminated dots 504. The real-time image and position 508 of the retro-reflective markers are also displayed on the video display device 412 as illuminated dots 508 (shown in FIG. 5 as "x" marks) which are preferably of a different shape or color than the image of the reference coordinates 504. The real-time image 510 of the patient may also be displayed. In an embodiment, the reference image 506 of the patient can also displayed on the video display device 412. The reference image 506 can be switched in to replace the real-time image 510 of the patient so that only a single image of the patient is displayed at any point in time, although both the reference and real-time positions of the markers are simultaneously displayed. Alternatively, the reference image 506 can be overlaid or superimposed over the real-time image 510 of the patient, so that both sets of images of the patient are displayed at the same time. The real-time nature of the image display allows any movement of the markers or particular body locations on the patient to be immediately displayed on the video display device 412. Thus, the image on the video display device 412 can be used to assist the correction of posture and absolute position errors. For example, the simultaneous display of both the reference and real-time positions for the markers allows a therapist to visually determine adjustments needed to line up the two sets of marker images to correct position errors. Moreover, the display of the reference and real-time images of the patient allows a therapist to visually determine adjustments needed to correct posture errors.

Figure 6A:
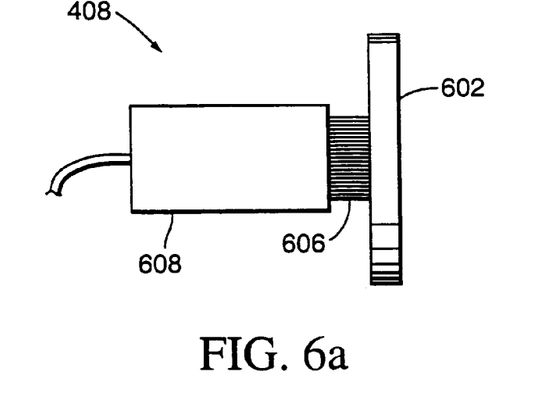
FIG. 6a is a side view of a camera that can be employed with the invention.
Figure 6B:
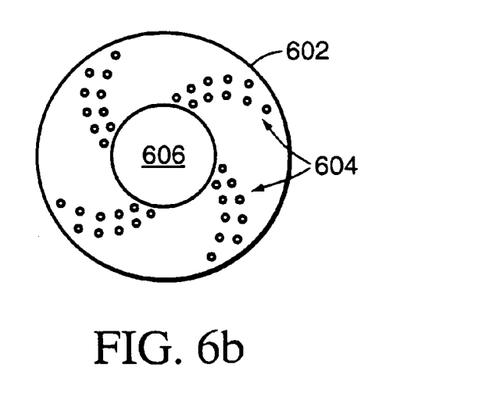

FIGS. 6a and 6b depict an embodiment of a camera 408 that can used in the present invention. Camera 408 is a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focussed on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 410 to process the video image and to calculate the positions of the retro-reflective markers 406. According to an embodiment of the invention, camera 408 is a monochrome CCD camera having RS-170 output and 640×480 pixel resolution. Alternatively, camera 408 can comprise a CCD camera having CCIR output and 756×567 pixel resolution.

In a particular embodiment of the invention, an infra-red illuminator 602 ("IR illuminator") is co-located with camera 408. IR illuminator 602 produces one or more beams of infrared light that is directed in the same direction as camera 408. IR illuminator 602 comprises a surface that is ringed around the lens 606 of camera body 608. The surface of IR illuminator 602 contains a plurality of individual LED elements 604 for producing infrared light. The LED elements 604 are arranged in a spiral pattern on the IR illuminator 602. Infrared filters that may be part of the camera 408 are removed or disabled to increase the camera's sensitivity to infrared light.

The position and orientation of cameras 408 should be calibrated to ensure that the absolute coordinates of retro-reflective markers 406 are properly calculated. To calibrate the camera 408, a reference target is placed on the treatment table in a specified location. The reference target contains a set of well-defined target elements at known heights and orientations. The data recorded by the cameras 408 for the reference target is used to perform precise position and orientation calibrations. More information regarding the calibration of multiple cameras in a video/optical imaging system can be found in "Close-range Camera Calibration", *Photogrammetric Engineering*, 37, 855–866 (1971) and *The Handbook of Non-Topographic Photogrammetry*, $2^{nd}$ ed., American Society of Photogrammetry and Remote Sensing (1989), both of which are hereby incorporated by reference.

Figure 7A:
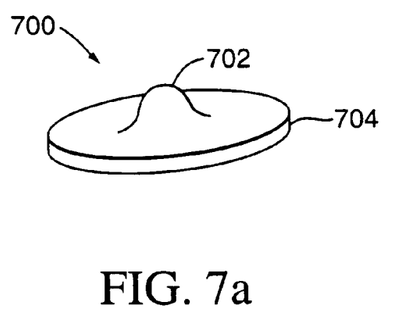
FIG. 7a is a cross-sectional view of a retro-reflective marker that can be utilized in the invention.
Figure 7B:
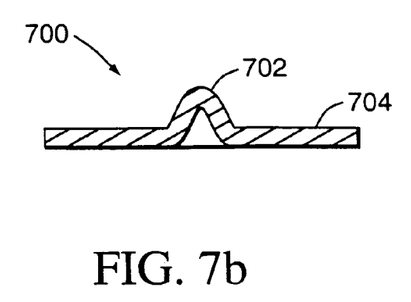

FIGS. 7a and 7b depict an embodiment of a retro-reflective marker 700 that can be employed within the present invention. Retro-reflective marker 700 comprises a raised reflective surface 702 for reflecting light. Raised reflective surface 702 preferably comprises an approximate semi-spherical shape such that light can be reflected regardless of the input angle of the light source. A flat surface 704 surrounds the raised reflective surface. The underside of flat surface 704 provides a mounting area to attach retro-reflective marker 700 to particular locations on a patient's body. According to an embodiment, retro-reflective marker 406 is comprised of a retro-reflective material 3M#7610WS available from 3M Corporation. In an embodiment, retro-reflective marker 700 has a diameter of approximately 0.5 cm and a height of the highest point of raised reflective surface 702 of approximately 0.1 cm.

Figure 8:
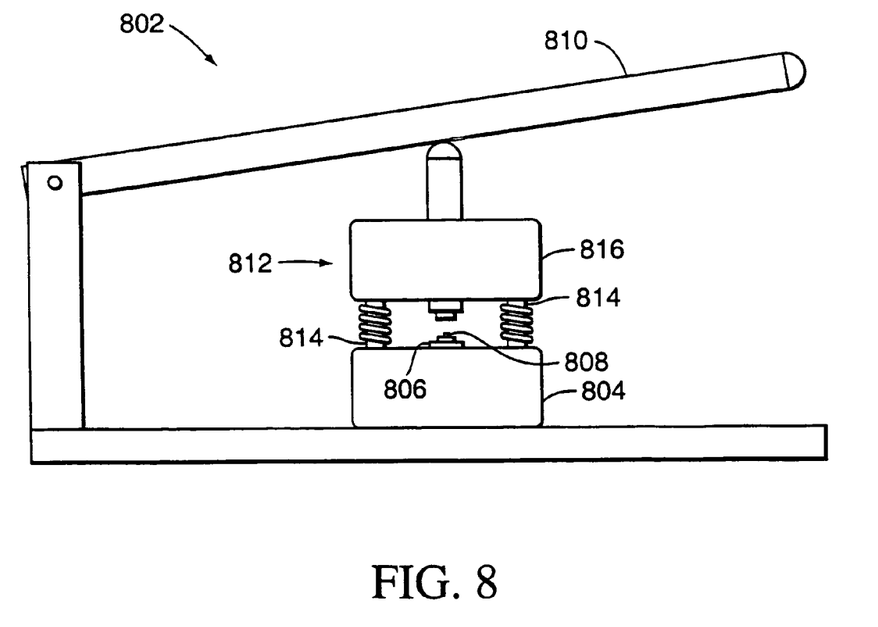
FIG. 8 depicts an apparatus that can be employed to manufacture the retro-reflective marker of FIGS. 7a and 7b.

FIG. 8 depicts an apparatus 802 that can be employed to manufacture retro-reflective markers 700. Apparatus 802 comprises a base portion 804 having an elastic ring 806 affixed thereto. Elastic ring 806 is attached to bottom mold piece 808 having a bulge protruding from its center. A control lever 810 can be operated to move top portion 812 along support rods 814. Top portion 812 comprises a spring-loaded top mold piece 814. Top mold piece 814 is formed with a semi-spherical cavity on its underside. In operation, a piece of retro-reflective material is placed on bottom mold piece 808. Control lever 810 is operated to move top portion 812 towards base portion 804. The retro-reflective material is compressed and shaped between the bottom mold piece 808 and the top mold piece 814. The top mold piece 814 forms the upper exterior of the retro-reflective material into a semi-spherical shape.

In an alternate embodiment, marker 406 comprises a marker block having one or more reference locations on its surface. Each reference location on the marker block preferably comprises a retro-reflective or reflective material that is detectable by an optical imaging apparatus, such as camera 408.

Figure 9:
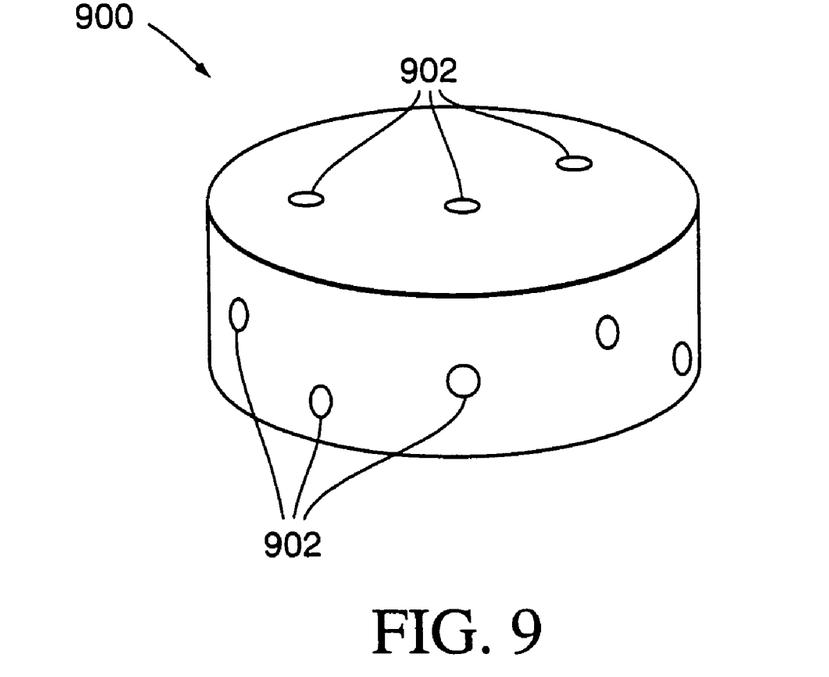
FIG. 9 depicts an embodiment of a marker block.

FIG. 9 depicts an embodiment of a marker block 900 having a cylindrical shape with multiple reference locations comprised of retro-reflective elements 902 located on its surface. Marker block 900 can be formed as a rigid block (e.g., from styrofoam). Blocks made in this fashion can be reused a plurality of times, even with multiple patients. The retro-reflective elements 902 can be formed from the same material used to construct retro-reflective markers 406 of FIGS. 7a and 7b. The marker block is preferably formed from a material that is light-weight enough not to interfere with normal breathing by the patient.

One advantage to using a marker block such as marker block 900, is that with a-priori knowledge of the relative positions of the reference locations/retro-reflective elements 902 on the marker block 900, it is possible to determine all six degrees of freedom of the marker block from a single camera view. In other words, only a single camera is required to derive the absolute coordinates of a marker block 900. This results because the relative positioning between the retro-reflective elements 902 on the surface of marker block 900 are known, and the absolute coordinates and viewing orientation of the camera 408 are also known. The detected image of the marker block 900 by camera 408 indicates the positioning of the visible reference locations/retro-reflective elements 902 relative to the camera's viewing orientation. Because the actual relative positions between the retro-reflective elements 502 are known, the detected relative coordinates of the visible retro-reflective elements 902 from the camera image can be used to derive the absolute coordinate of the marker block 900.

Figure 10:
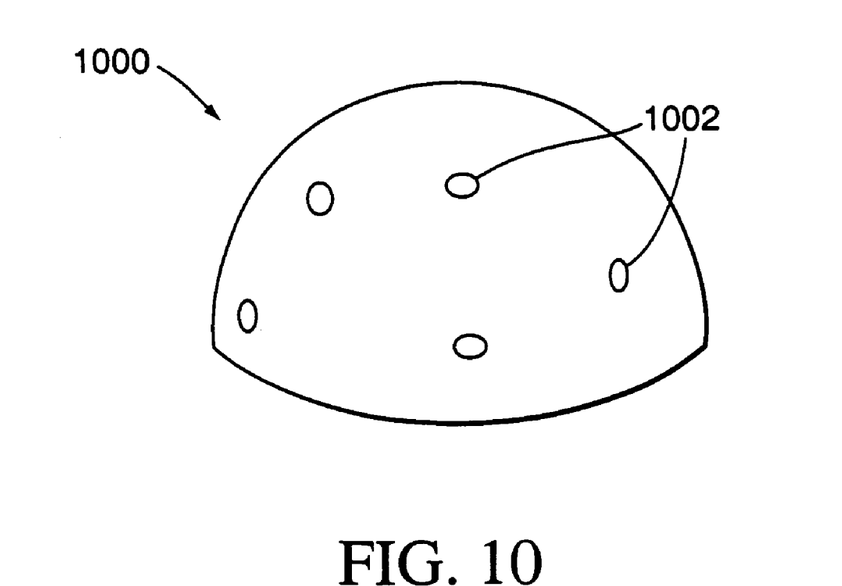
FIG. 10 depicts an alternate marker block.

A marker block can be formed into any shape or size, as long as the size, spacing, and positioning of the reference locations are configured such that a camera or other optical imaging apparatus can view and generate an image that accurately shows the positioning of at least two/three or more of the reference locations. For example, FIG. 10 depicts an alternate marker block 1000 having a hemispherical shape comprised of a plurality of retro-reflective elements 1002 attached to its surface.

The marker block can be formed with shapes to fit particular body parts. For example, molds or casts that match to specific locations on the body can be employed as marker blocks. Marker blocks shaped to fit certain areas of the body facilitate the repeatable placement of the marker blocks at particular locations on the patient. Alternatively, the marker blocks can be formed to fit certain fixtures that are attached to a patient's body. For example, a marker block can be formed within indentations and grooves that allow it to be attached to eyeglasses. In yet another embodiment, the fixtures are formed with integral marker block(s) having reflective or retro-reflective markers on them.

An alternate embodiment of the marker block comprises only a single reference location/reflective element on its surface. This embodiment of the marker block is used in place of the retro-reflective marker 406 to detect particular locations on a patient's body with an optical imaging apparatus.

In the foregoing specification, the invention has been described with reference to specific embodiments thereof. It will, however, be evident that various modifications and changes may be made thereto without departing from the broader spirit and scope of the invention. For example, the coordinates for various body locations on a patient can be obtained by generating images of particular landmarks on a patient body, rather than using reflective or retro-reflective markers. The specification and drawings are, accordingly, to be regarded in an illustrative rather than restrictive sense.

The invention claimed is:

1. A marker system for use in a patient treatment system comprising:
    a marker block having a surface;
    a first reference location on the surface;
    a second reference location on the surface, and spaced apart from the first reference location; and the first reference location and the second reference location positioned on the surface such that both reference locations are simultaneously detectable by an optical imaging apparatus.

2. The system of claim 1 in which the first and second reference locations comprise rerro-reflective material.

3. The system of claim 1, wherein said surface is a portion of a structure sized to fit a patient body location.

4. The system of claim 1, further comprising said optical imaging apparatus.

5. The marker system of claim 1, wherein the marker block is a non-surgical instrument.

6. A marker system, comprising.
a marker block having a surface;
two or more reflective elements located on said surface, said two or more reflective elements having known positioning relative to each other, wherein one of said two or more reflective elements is spaced apart from another of said two or more reflective elements; and
said marker block positioned such that at least two of said two or more reflective elements are viewable by one or more optical imaging apparatus.

7. The system of claim 6 in which one of the two or more reflective elements comprises a hemispherical shape.

8. The system of claim 6 in which said two or more reflective elements are retro-reflective elements.

9. The system of claim 6 in which said marker block is shaped to fit a specific body location.

10. The system of claim 6 further comprising one or more optical imaging apparatus and a computing device to receive output information from said one or more optical imaging apparatus, the computing device having a processor configured to determine the position and orientation of said marker block based on the information.

11. The system of claim 6 further comprising a video display device to display a video image of a patient.

12. The system of claim 11 which said video image comprises real-time images of said marker block.

13. The system of claim 11 in which said video image comprises real-dine images of said patient.

14. The system if claim 6, further comprising said one or more optical imaging apparatus.

15. The marker system of claim 6, wherein the marker block is a non-surgical instrument.

16. The system of claim 14 in which absolute coordinate of said one or more optical imaging apparatus is known.

17. The system of claim 14 in which viewing orientation of said one or more optical imaging apparatus is known.

18. The system of claim 14 in which absolute coordinate of said one or more optical imaging apparatus is known.

19. The system of claim 14 in which said one or more optical imaging apparatus comprises CCD cameras.

* * * * *

UNITED STATES PATENT AND TRADEMARK OFFICE
CERTIFICATE OF CORRECTION

PATENT NO. : 7,204,254 B2
APPLICATION NO. : 09/940679
DATED : April 17, 2007
INVENTOR(S) : Majid L. Riaziat et al.

It is certified that error appears in the above-identified patent and that said Letters Patent is hereby corrected as shown below:

IN THE CLAIMS:
Column 13, Claim 2 should read:
--The system of claim 1 in which the first and second reference locations comprise ~~rerro-reflective~~ retro-reflective material.

Column 14, Claim 13 should read:
--The system of claim 11 in which said video image comprises ~~real-dine~~ real-time images of said patient.

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,204,254 B2 |
| APPLICATION NO. | : 09/940679 |
| DATED | : April 17, 2007 |
| INVENTOR(S) | : Majid L. Riaziat et al. |

It is certified that error appears in the above-identified patent and that said Letters Patent is hereby corrected as shown below:

IN THE CLAIMS:
Column 13, Claim 2, lines 5 and 6 should read:
--The system of claim 1 in which the first and second reference locations comprise ~~rerro-reflective~~ retro-reflective material.

Column 14, Claim 13, lines 12 and 13 should read:
--The system of claim 11 in which said video image comprises ~~real-dine~~ real-time images of said patient.

This certificate supersedes the Certificate of Correction issued May 20, 2008.

Signed and Sealed this

Seventeenth Day of June, 2008

JON W. DUDAS
*Director of the United States Patent and Trademark Office*